(12) United States Patent  
Parham et al.

(10) Patent No.: US 8,597,798 B2
(45) Date of Patent: Dec. 3, 2013

(54) MATERIALS FOR ORGANIC ELECTROLUMINESCENT DEVICES

(75) Inventors: Amir Hossain Parham, Frankfurt (DE); Arne Buesing, Frankfurt (DE); Anja Gerhard, Veitschöchheim (DE); Joachim Kaiser, Darmstadt (DE); Rocco Fortte, Frankfurt (DE)

(73) Assignee: Merck Patent GmbH (DE)

( * ) Notice: Subject to any disclaimer, the term of this patent is extended or adjusted under 35 U.S.C. 154(b) by 369 days.

(21) Appl. No.: 13/001,234

(22) PCT Filed: Oct. 15, 2009

(86) PCT No.: PCT/EP2009/007407
§ 371 (c)(1),
(2), (4) Date: Dec. 23, 2010

(87) PCT Pub. No.: WO2010/054731
PCT Pub. Date: May 20, 2010

(65) Prior Publication Data
US 2011/0095281 A1 Apr. 28, 2011

(30) Foreign Application Priority Data
Nov. 13, 2008 (DE) .......................... 10 2008 057 050

(51) Int. Cl.
*H01L 51/54* (2006.01)
*C09K 11/06* (2006.01)

(52) U.S. Cl.
USPC .......... 428/690; 428/917; 313/504; 313/506; 252/301.16; 257/40; 257/E51.044; 546/4; 546/10; 548/103

(58) Field of Classification Search
None
See application file for complete search history.

(56) References Cited

U.S. PATENT DOCUMENTS

| | | | |
|---|---|---|---|
| 4,539,507 A | 9/1985 | VanSlyke et al. |
| 5,151,629 A | 9/1992 | VanSlyke |
| 5,621,131 A | 4/1997 | Kreuder et al. |
| 6,653,438 B1 | 11/2003 | Spreitzer et al. |
| 7,345,301 B2 | 3/2008 | Gerhard et al. |
| 7,442,797 B2 | 10/2008 | Itoh et al. |
| 7,659,540 B2 | 2/2010 | Heun et al. |
| 7,701,131 B2 | 4/2010 | Gerhard et al. |
| 7,723,455 B2 | 5/2010 | Becker et al. |
| 7,795,801 B2 | 9/2010 | Ueda et al. |
| 7,834,136 B2 | 11/2010 | Parham et al. |
| 2005/0069729 A1 | 3/2005 | Ueda et al. |
| 2006/0134461 A1 | 6/2006 | Huo et al. |
| 2006/0243966 A1 | 11/2006 | Sotoyama et al. |
| 2006/0255332 A1 | 11/2006 | Becker et al. |
| 2006/0284140 A1 | 12/2006 | Breuning et al. |
| 2007/0075311 A1 | 4/2007 | Okada |
| 2007/0082284 A1 | 4/2007 | Stoessel et al. |
| 2007/0176147 A1 | 8/2007 | Buesing et al. |
| 2007/0205714 A1 | 9/2007 | Busing et al. |
| 2008/0038586 A1 | 2/2008 | Nishizeki et al. |
| 2009/0134384 A1 | 5/2009 | Stoessel et al. |
| 2009/0167166 A1 | 7/2009 | Bach et al. |
| 2009/0226759 A1 | 9/2009 | Heun et al. |
| 2009/0302742 A1 | 12/2009 | Komori et al. |
| 2009/0302752 A1 | 12/2009 | Parham et al. |
| 2010/0102305 A1 | 4/2010 | Heun et al. |
| 2010/0187977 A1 | 7/2010 | Kai et al. |
| 2010/0244009 A1 | 9/2010 | Parham et al. |
| 2010/0288974 A1 | 11/2010 | Buesing et al. |
| 2011/0068304 A1 | 3/2011 | Parham et al. |

FOREIGN PATENT DOCUMENTS

| | | |
|---|---|---|
| DE | 102008033943 A1 | 1/2010 |
| DE | 102008036982 A1 | 2/2010 |
| DE | 102008056688 A1 | 5/2010 |
| EP | 652273 A1 | 5/1995 |
| EP | 707020 A2 | 4/1996 |
| EP | 842208 A1 | 5/1998 |
| EP | 894107 A1 | 2/1999 |
| EP | 1028136 | 8/2000 |
| EP | 1205527 A1 | 5/2002 |
| EP | 1617710 A1 | 1/2006 |
| EP | 1617711 A1 | 1/2006 |
| EP | 1731584 A1 | 12/2006 |
| JP | 2004-288381 A | 10/2004 |
| JP | 2005-347160 A | 12/2005 |
| WO | WO-92/18552 A1 | 10/1992 |
| WO | WO-00/22026 A1 | 4/2000 |
| WO | WO-2004/013080 A1 | 2/2004 |
| WO | WO-2004/041901 A1 | 5/2004 |
| WO | WO-2004/070772 A2 | 8/2004 |
| WO | WO-2004/093207 A2 | 10/2004 |
| WO | WO-2004/108857 A1 | 12/2004 |
| WO | WO-2004/113412 A2 | 12/2004 |
| WO | WO-2004/113468 A1 | 12/2004 |
| WO | WO-2005/003253 A2 | 1/2005 |
| WO | WO-2005/011013 A1 | 2/2005 |
| WO | WO-2005/014689 A2 | 2/2005 |
| WO | WO-2005/039246 A1 | 4/2005 |
| WO | WO-2005/040302 A1 | 5/2005 |
| WO | WO-2005/042444 A2 | 5/2005 |
| WO | WO-2005/042550 A1 | 5/2005 |
| WO | WO-2005/104264 A1 | 11/2005 |
| WO | WO-2005/111172 A2 | 11/2005 |

(Continued)

*Primary Examiner* — Michael H Wilson
(74) *Attorney, Agent, or Firm* — Novak Druce Connolly Bove + Quigg LLP

(57) ABSTRACT

The present invention relates to transition-metal complexes of the general formula I or II, in particular as emitter molecules in organic electronic devices, to a layer and an electronic device which comprise the compounds according to the invention, and to a process for the preparation of the compounds according to the invention.

15 Claims, No Drawings

(56) References Cited

FOREIGN PATENT DOCUMENTS

| | | |
|---|---|---|
| WO | WO-2006/005627 A1 | 1/2006 |
| WO | WO-2006/061181 A1 | 6/2006 |
| WO | WO-2006/098120 A1 | 9/2006 |
| WO | WO-2006/117052 A1 | 11/2006 |
| WO | WO-2007/017066 A1 | 2/2007 |
| WO | WO-2007/063754 A1 | 6/2007 |
| WO | WO-2007/137725 A1 | 12/2007 |
| WO | WO-2008/056746 A1 | 5/2008 |
| WO | WO-2008/066192 A1 | 6/2008 |
| WO | WO-2008/086851 A1 | 7/2008 |
| WO | WO-2009/062578 A1 | 5/2009 |
| WO | WO-2010/006680 | 1/2010 |
| WO | WO-2010/015306 | 2/2010 |
| WO | WO-2010/054729 | 5/2010 |

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2009/007407, filed Oct. 15, 2009, which claims benefit of German application 10 2008 057 050.8, filed Nov. 13, 2008.

BACKGROUND OF THE INVENTION

The present invention relates to transition-metal complexes of the general formula I or II, in particular as emitter molecules in organic electronic devices, to a layer and an electronic device which comprise the compounds according to the invention, and to a process for the preparation of the compounds according to the invention.

Chelate complexes and organometallic compounds are used as functional materials in a number of applications of different types which can be ascribed to the electronics industry in the broadest sense. In the case of organic electroluminescent devices based on organic components (general description of the structure cf. U.S. Pat. Nos. 4,539,507 and 5,151,629) and individual components thereof, the organic light-emitting diodes (OLEDs), the market introduction has already taken place. In spite of the successes that have already been achieved, further improvements are still desirable here.

In recent years, organometallic complexes which exhibit phosphorescence instead of fluorescence have increasingly been under discussion (M. A. Baldo, S. Lamansky, P. E. Burrows, M. E. Thompson, S. R. Forrest, Appl. Phys. Lett., 1999, 75, 4-6). For theoretical spin-statistical reasons, an up to fourfold increase in energy and power efficiency is possible using organometallic compounds as phosphorescence emitters. The main conditions that should be mentioned here for practical use are, in particular, a long operating lifetime, high stability to temperature stresses and a low use and operating voltage in order to facilitate mobile applications.

Besides the individual specific weak points for each material, the class of known metal complexes has a general need for improvement, which is described briefly below:

Many of the known metal complexes have low thermal stability (cf.: R. G. Charles, J. Inorg. Nucl. Chem., 1963, 25, 45). On vacuum deposition, this inevitably always results in the liberation of organic pyrolysis products, which, in some cases even in small amounts, considerably shorten the operating lifetime of OLEDs.

The strong interaction of the complex units in the solid, in particular in the case of planar complexes of $d^8$ metals, such as platinum(II), likewise causes aggregation of the complex units in the emitter layer if the degree of doping exceeds about 0.1%, which is the case in accordance with the current prior art. This aggregation results in the formation of so-called excimers or exciplexes on excitation (optical or electrical). These aggregates frequently have an unstructured, broad emission band, which makes the generation of pure primary colours (RGB) considerably more difficult or completely impossible. In general, the efficiency for this transition also drops.

In addition, it is evident from the above-said that the emission colour is highly dependent on the degree of doping, a parameter which can be controlled precisely only with considerable technical effort, in particular in large production plants.

Known in OLED technology are metal complexes of the group 10 transition metals (Ni, Pd, Pt) in which the central metal is bonded via two aromatic N atoms and two C atoms (WO 2004/108857, WO 2005/042550, WO 2005/042444, US 2006/0134461 A1) or two imine-like N atoms in combination with two phenolic O atoms (WO 2004/108857) or via two aromatic N atoms and two basic N atoms (WO 2004/108857). The known compounds have, inter alia, electroluminescence in the blue, red and green region of the electromagnetic spectrum.

Nevertheless, there is still a demand for further compounds which do not have the above-mentioned disadvantages and preferably exhibit electroluminescence in the blue, red and green region of the electromagnetic spectrum and in particular can also be employed in the solid state as light-emitting layer.

BRIEF SUMMARY OF THE INVENTION

The object of the invention was thus to provide compounds of this type.

Surprisingly, it has been found that a long operating lifetime is achieved by metal complexes having imine-like N atoms in combination with aromatic C atoms or olefinic C atoms in combination with aromatic N atoms as phosphorescence emitters in OLEDs and high stability to temperature stresses and a low use and operating voltage are achieved by bridging these ligands.

The present invention provides in this respect a compound of the general formula I

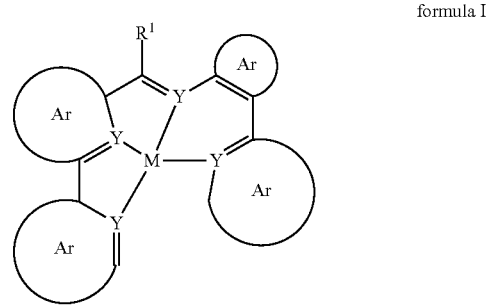

formula I where

M is a metal ion in oxidation state +2,

Ar is, identically or differently on each occurrence, an aromatic or heteroaromatic ring system, which may be substituted by one or more radicals R of any desired type, and the ring systems Ar may optionally be linked to one another by single bonds or any desired radicals R, Y is, identically or differently on each occurrence, C, N or P, with the proviso that either two C atoms and two N atoms or two C atoms and two P atoms are always bonded to the metal, $R^1$ is any desired radical.

DETAILED DESCRIPTION OF THE INVENTION

The present invention furthermore provides a compound of the general formula II

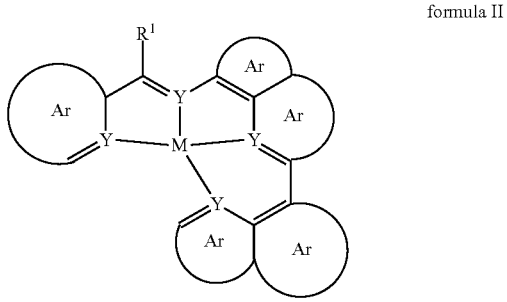

formula II where
M is a metal ion in oxidation state +2,
Ar is, identically or differently on each occurrence, an aromatic or heteroaromatic ring system, which may be substituted by one or more radicals R of any desired type, and the ring systems Ar may optionally be linked to one another by single bonds or any desired radicals R,
Y is, identically or differently on each occurrence, C, N or P, with the proviso that either two C atoms and two N atoms or two C atoms and two P atoms are always bonded to the metal,
$R^1$ is any desired radical.

In a preferred embodiment of the invention, in the compounds of the general formula I or II,
Ar is, identically or differently on each occurrence, an aromatic or heteroaromatic ring system, which may be substituted by one or more radicals R of any desired type, and the ring systems Ar may optionally be linked to one another by single bonds or any desired radicals R,
R is, identically or differently on each occurrence, H, D, F, Cl, Br, I, $N(Ar^1)_2$, $N(R^2)_2$, CN, $NO_2$, $Si(R^2)_3$, $B(OR^2)_2$, $C(=O)Ar^1$, $C(=O)R^2$, $P(=O)(Ar^1)_2$, $P(=O)(R^2)_2$, $S(=O)R^1$, $S(=O)R^2$, $S(=O)_2Ar^1$, $S(=O)_2R^2$, $CR^2=CR^2Ar^1$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems, where two or more substituents R may also form a mono- or polycyclic, aliphatic or aromatic ring system with one another,
$Ar^1$ is, identically or differently on each occurrence, an aromatic or heteroaromatic ring system having 5 to 40 aromatic ring atoms, which may be substituted by one or more non-aromatic radicals,
$R^1$ is, identically or differently on each occurrence, H, D, F, $CF_3$, CN, an alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems, where $R^1$ may also form a mono- or polycyclic, aliphatic or aromatic ring system with R,
$R^2$ is, identically or differently on each occurrence, H, D, F, CN or an aliphatic, aromatic and/or heteroaromatic hydrocarbon radical having 1 to 20 C atoms, in which, in addition, one or more H atoms may be replaced by F, where two or more substituents $R^2$ also form a mono- or polycyclic, aliphatic or aromatic ring system with one another.

In a further preferred embodiment of the invention, M is equal to Pd or equal to Pt. M is particularly preferably equal to Pt.

In still a further preferred embodiment of the invention, in the compounds of the general formula I or II,
M is Pt,
Ar is, identically or differently on each occurrence, an aromatic or heteroaromatic ring system having 5 to 10 aromatic ring atoms, which may be substituted by a plurality of radicals R,
Y is, identically or differently on each occurrence, C or N, with the proviso that two C atoms and two N atoms are always bonded to the metal,
R is, identically or differently on each occurrence, H, $N(Ar^1)_2$, CN, a straight-chain alkyl group having 1 to 10 C atoms or an aromatic or heteroaromatic ring system having 5 to 15 aromatic ring atoms, each of which may be substituted by one or more radicals $R^2$,
$R^1$ is, identically or differently on each occurrence, H, D, CN, an alkyl group having 1 to 3 C atoms or an aromatic or heteroaromatic ring system having 5 to 10 aromatic ring atoms, each of which may be substituted by one or more radicals $R^2$,
$R^2$ is, identically or differently on each occurrence, H, F, CN or an aliphatic, aromatic and/or heteroaromatic hydrocarbon radical having 1 to 20 C atoms, where two or more substituents $R^2$ may also form a mono- or polycyclic, aliphatic or aromatic ring system with one another, and
$Ar^1$ is as defined above.

If the radicals defined above occur a number of times within one compound, the radicals may, independently of one another on each occurrence, be identical or different, corresponding to the respective definition.

The following general definitions are furthermore used within this invention:

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

For the purposes of this invention, the group Ar in the general formulae I and II is particularly preferably benzene, naphthalene, pyridine, pyrimidine, pyrazine, pyridazine, quinoline, isoquinoline, furan, thiophene, pyrrole, benzofuran, benzothiophene and indole, where benzene, naphthalene, pyridine, quinoline and isoquinoline are most preferred.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc. are also intended to be taken to be aromatic ring systems for the purposes of this invention, as are systems in which two or more aryl groups are interrupted, for example, by a linear or cyclic alkyl group or by a silyl group.

An aromatic or heteroaromatic ring system having 5-60 aromatic ring atoms, which may also in each case be substituted by the above-mentioned radicals $R^1$ and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, an aliphatic hydrocarbon radical or an alkyl group, which may typically contain 1 to 40 or also 1 to 20 C atoms, and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$; furthermore, one or more H atoms may also be replaced by F, Cl, Br, I, CN or $NO_2$, preferably F, Cl or CN, furthermore preferably F or Cl, particularly preferably F.

A preferred embodiment of the compounds of the formulae I and II are the compounds of the following formulae III and IV:

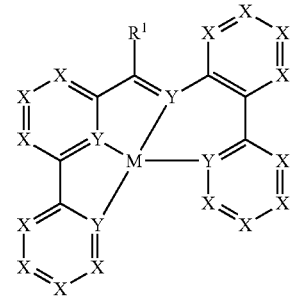

formula III

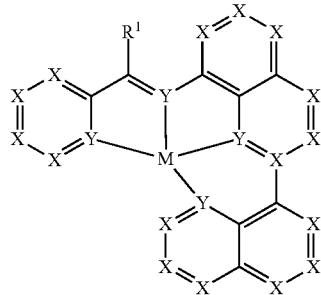

formula IV where M, Y, R and $R^1$ have the meaning mentioned above, and X stands for CR or N. It is preferred here for a maximum of two symbols X, particularly preferably a maximum of one symbol X, per ring to stand for N and for the other symbols X in this ring to stand for CR. Very particularly preferably, all groups X in a ring stand for CR.

Particularly preferred embodiments of the compounds mentioned above are the compounds of the following formulae V to XVI:

formula V
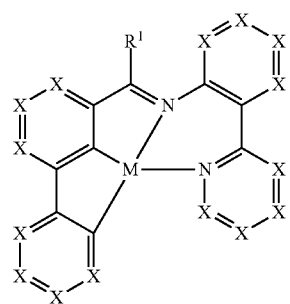
formula VI
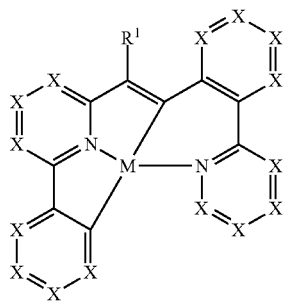
formula VII
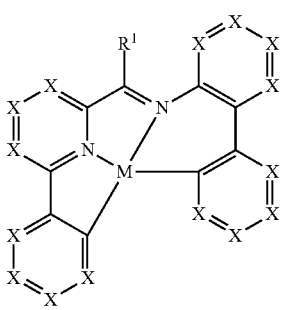
formula VIII
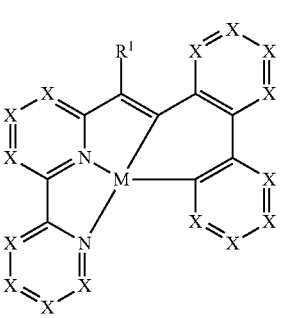
formula IX
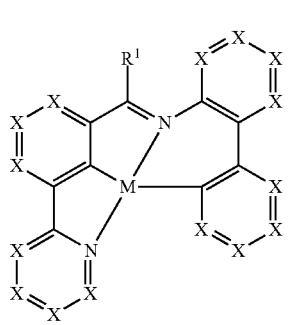
formula X
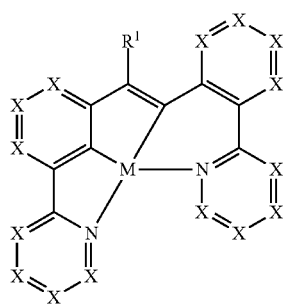
formula XI
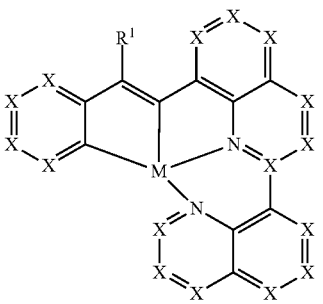
formula XII
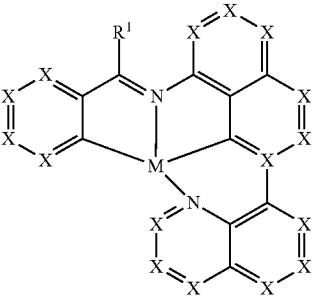
formula XIII
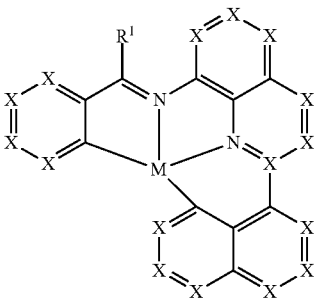
formula XIV
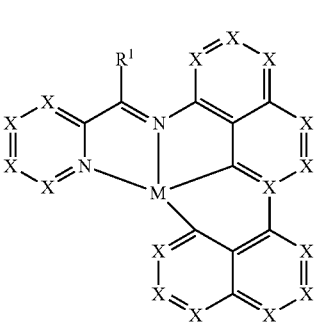

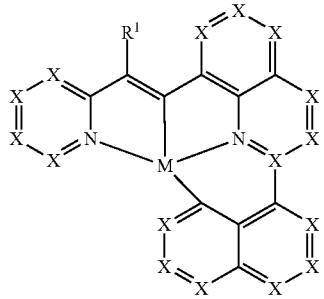
formula XV
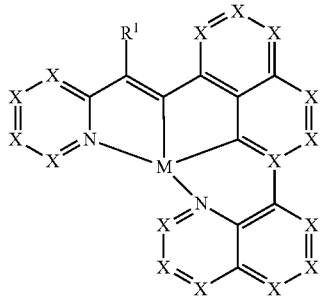
formula XVI
where the symbols used have the meanings mentioned above.
Besides the preferred compounds mentioned above, particular preference is furthermore given to the compounds shown in Table 1 below:
TABLE 1
Examples of compounds of the formulae I to XVI according to the invention
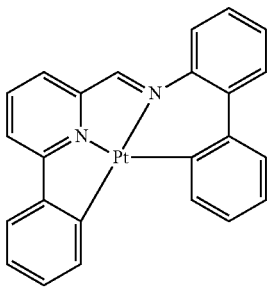
1
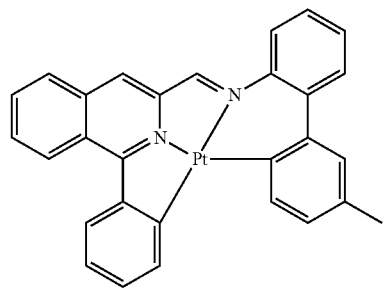
2
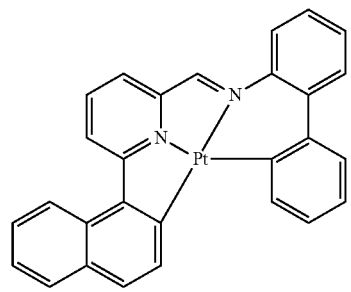
3

TABLE 1-continued
Examples of compounds of the formulae I to XVI according to the invention
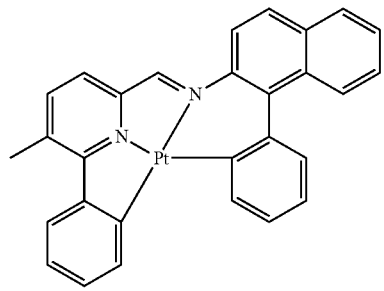
4
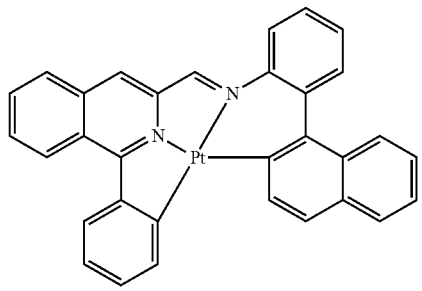
5
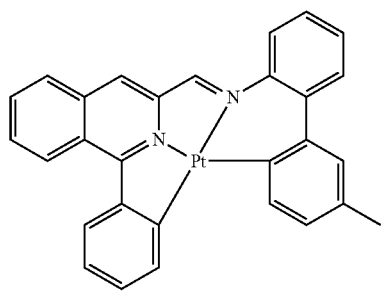
6
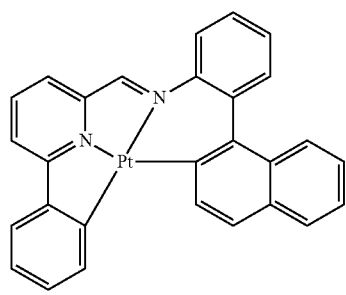
7

TABLE 1-continued
Examples of compounds of the formulae I to XVI according to the invention
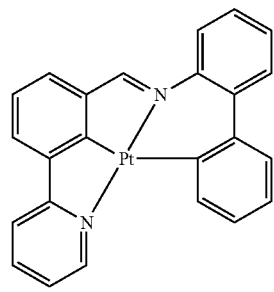
8
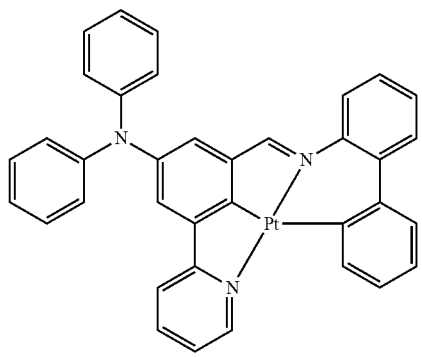
9
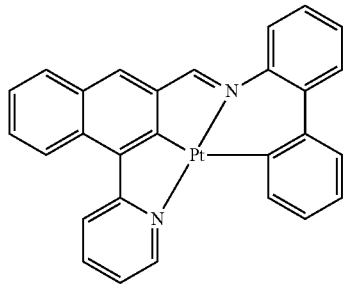
10
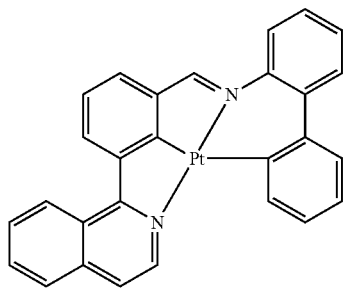
11

TABLE 1-continued
Examples of compounds of the formulae I to XVI according to the invention
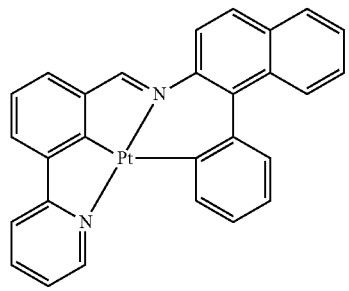
12
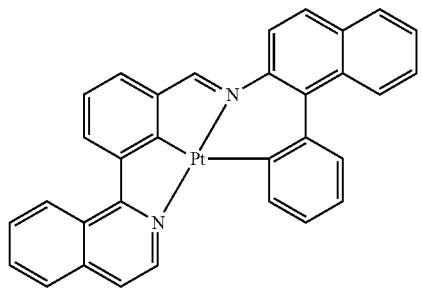
13
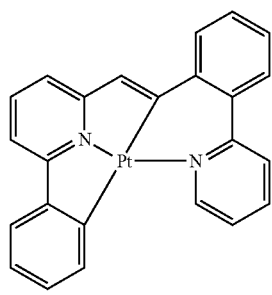
14
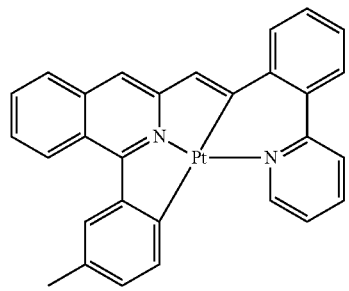
15

TABLE 1-continued
Examples of compounds of the formulae I to XVI according to the invention
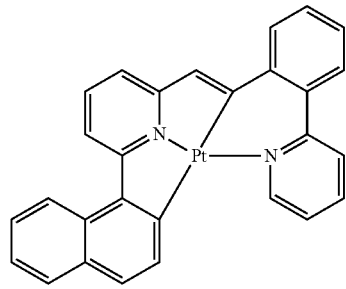
16
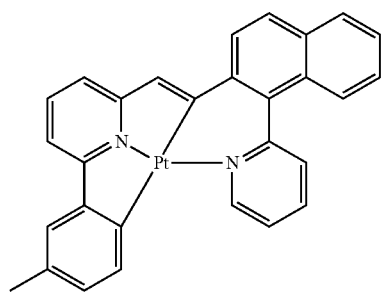
17
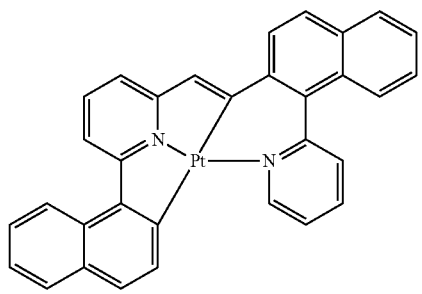
18
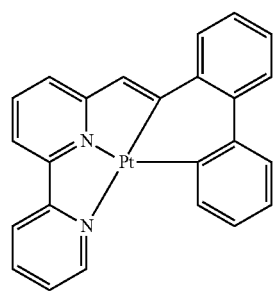
19

TABLE 1-continued
Examples of compounds of the formulae I to XVI according to the invention
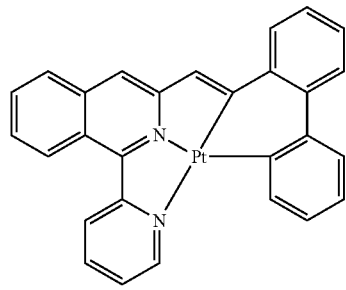
20
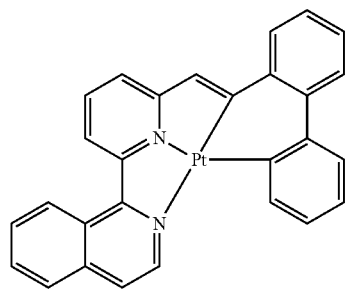
21
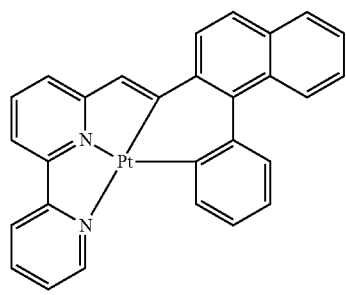
22
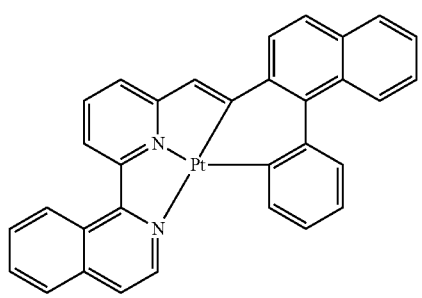
23

TABLE 1-continued
Examples of compounds of the formulae I to XVI according to the invention
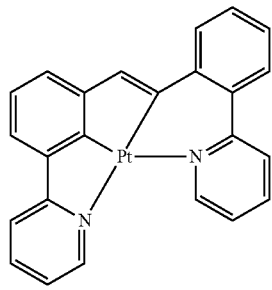
24
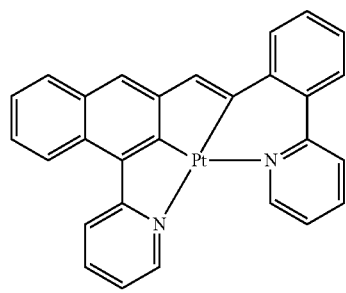
25
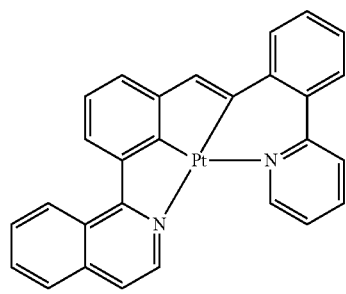
26
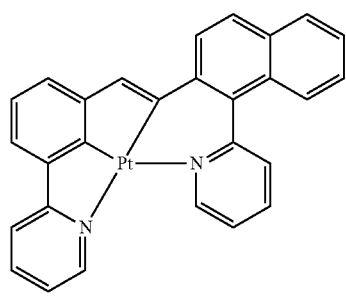
27

TABLE 1-continued
Examples of compounds of the formulae I to XVI according to the invention
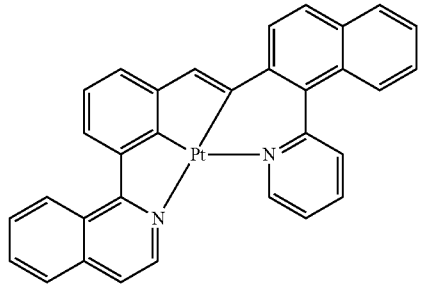
28
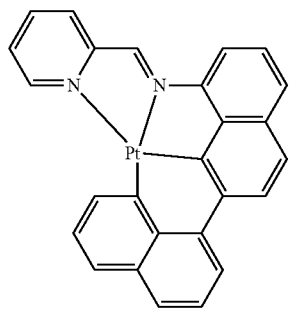
29
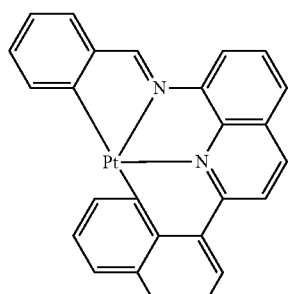
30
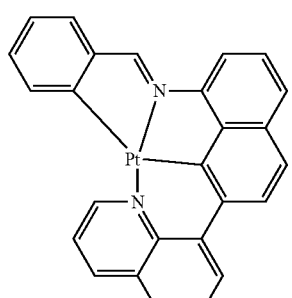
31

TABLE 1-continued
Examples of compounds of the formulae I to XVI according to the invention
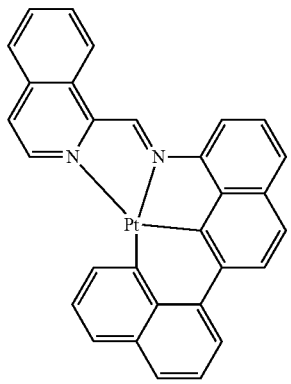
32
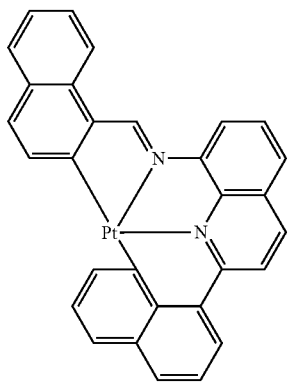
33
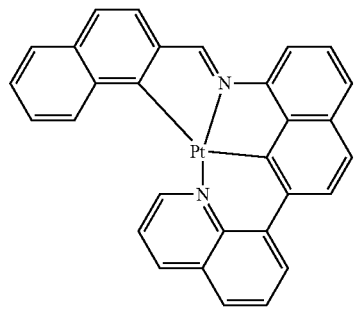
34
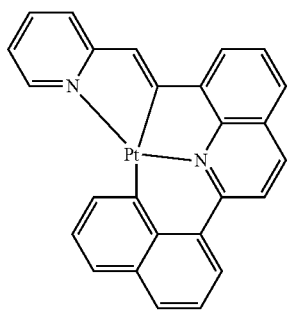
35

TABLE 1-continued
Examples of compounds of the formulae I to XVI according to the invention
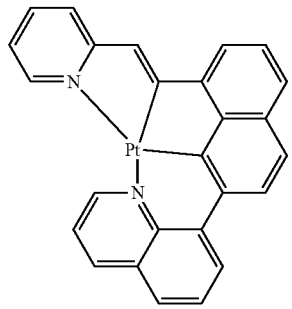
36
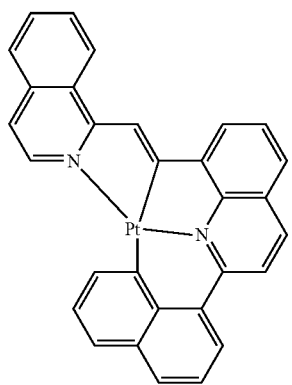
37
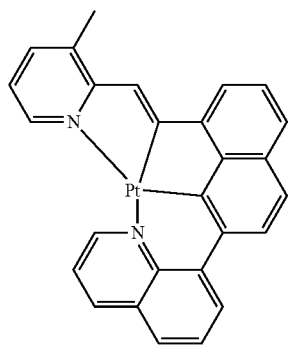
38
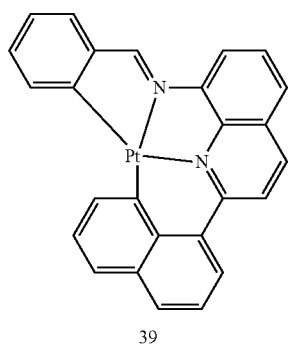
39

TABLE 1-continued
Examples of compounds of the formulae I to XVI according to the invention
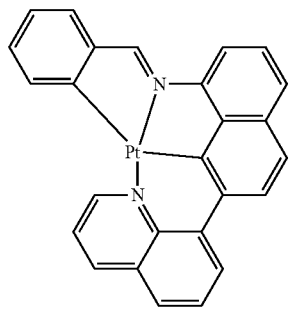
40
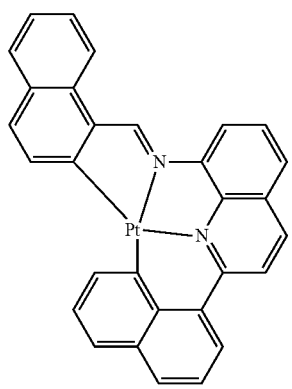
41
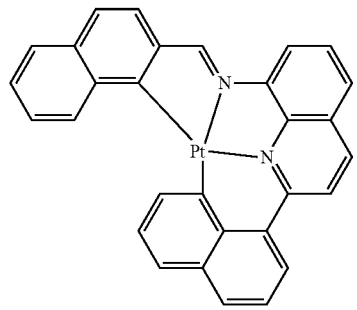
42
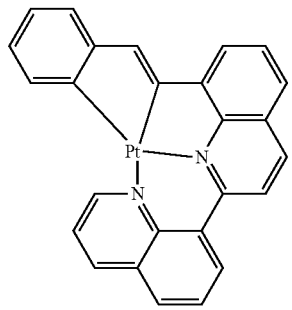
43

TABLE 1-continued
Examples of compounds of the formulae I to XVI according to the invention
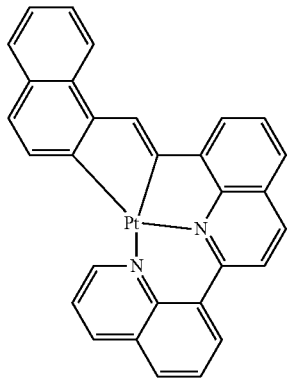
44
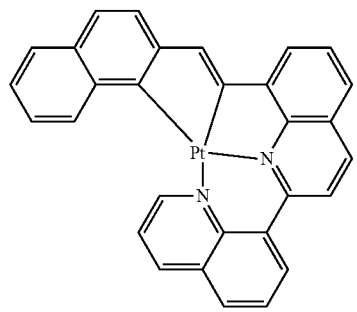
45
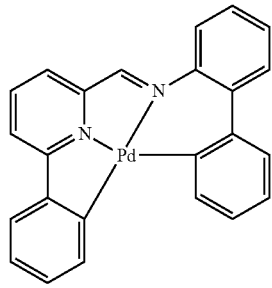
46
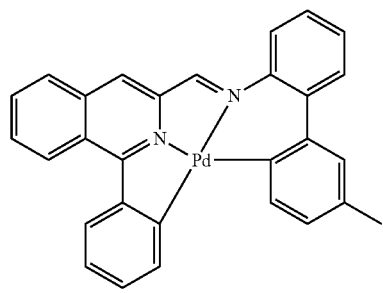
47

TABLE 1-continued
Examples of compounds of the formulae I to XVI according to the invention
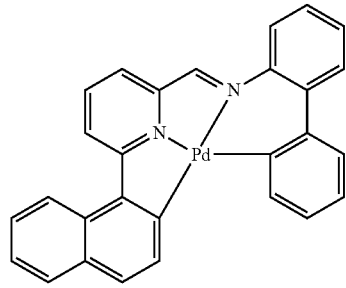
48
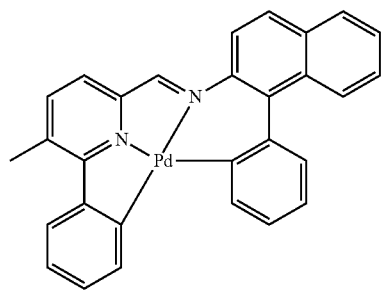
49
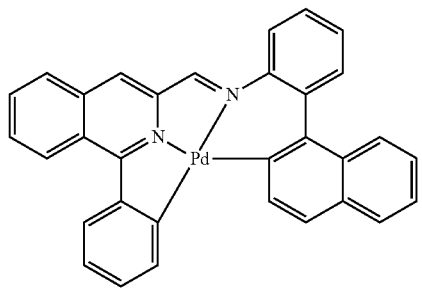
50
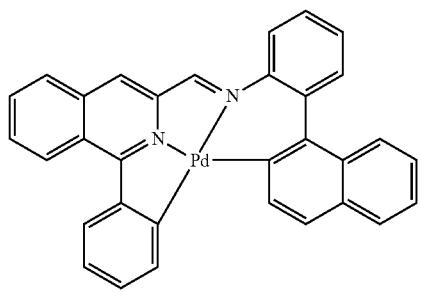
51

TABLE 1-continued
Examples of compounds of the formulae I to XVI according to the invention
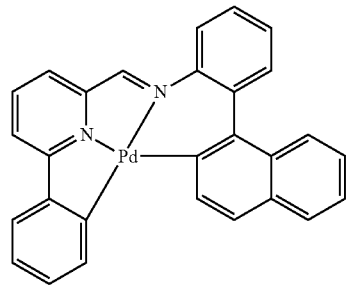
52
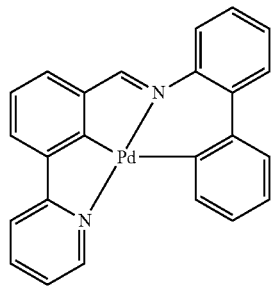
53
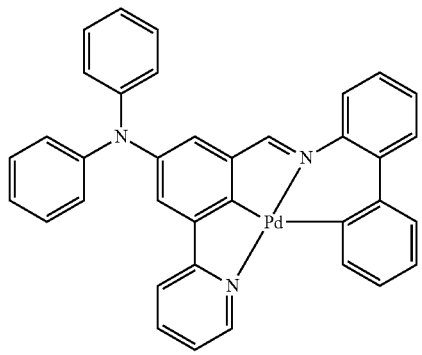
54
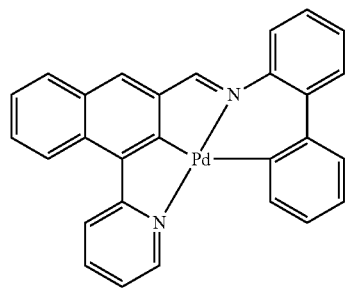
55

TABLE 1-continued
Examples of compounds of the formulae I to XVI according to the invention
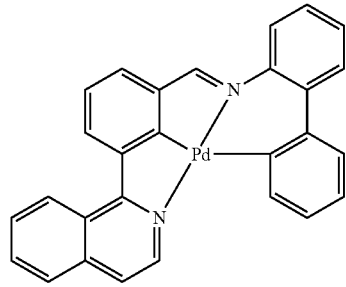
56
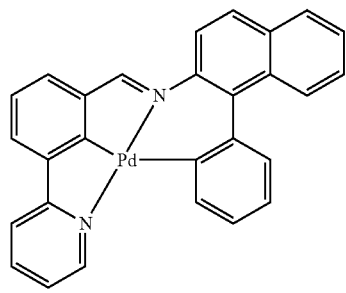
57
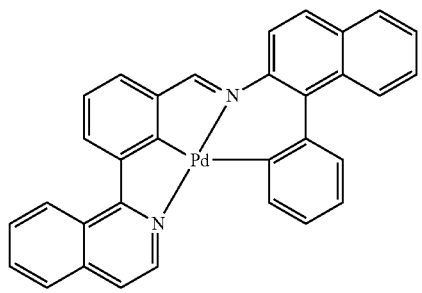
58
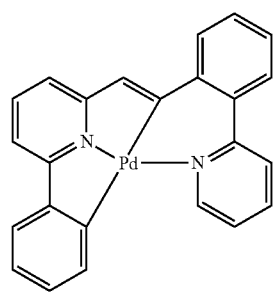
59

TABLE 1-continued
Examples of compounds of the formulae I to XVI according to the invention
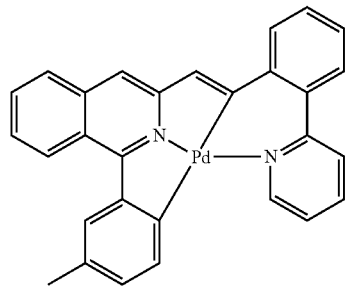
60
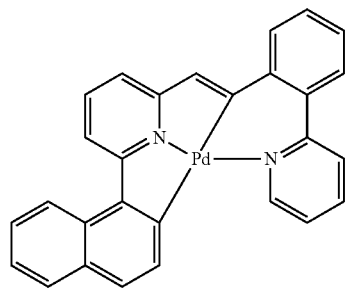
61
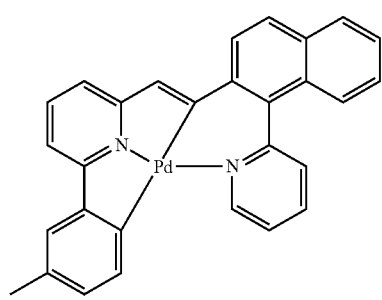
62
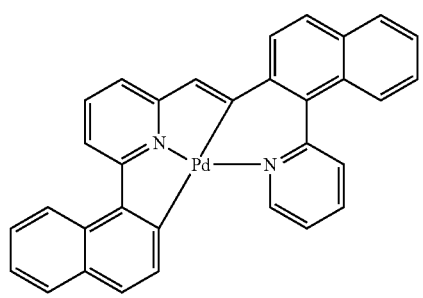
63

TABLE 1-continued
Examples of compounds of the formulae I to XVI according to the invention
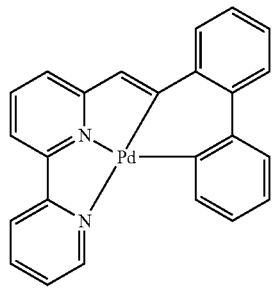
64
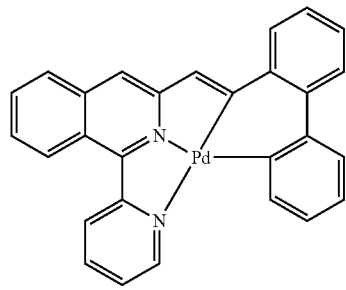
65
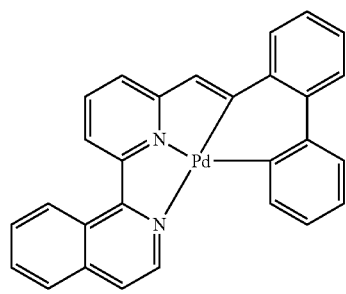
66
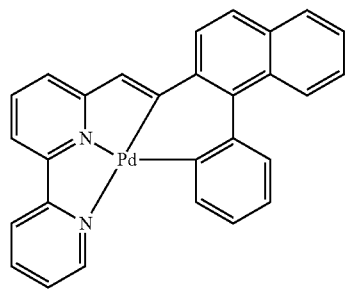
67

TABLE 1-continued
Examples of compounds of the formulae I to XVI according to the invention
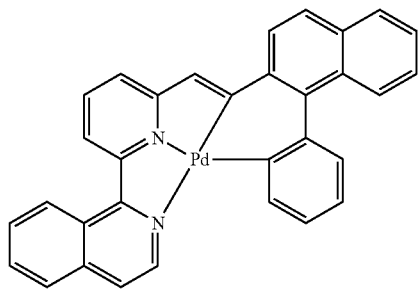
68
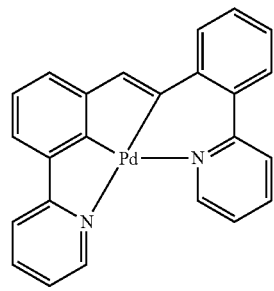
69
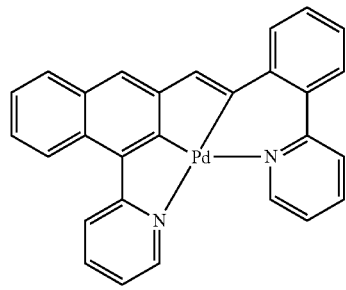
70
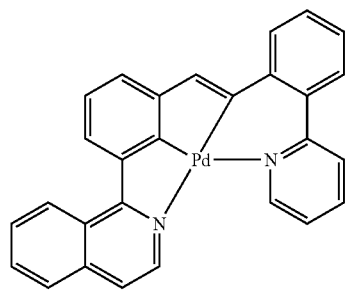
71

TABLE 1-continued
Examples of compounds of the formulae I to XVI according to the invention
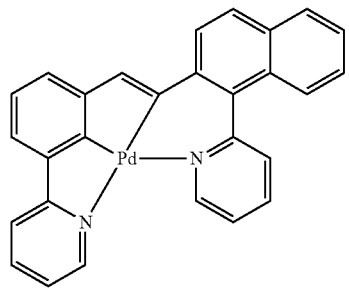
72
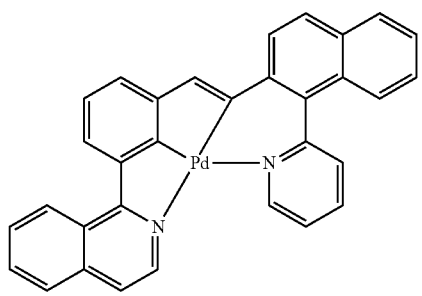
73
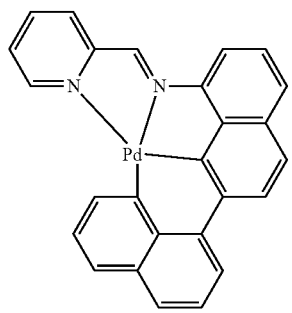
74
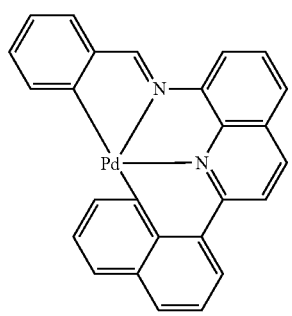
75

TABLE 1-continued
Examples of compounds of the formulae I to XVI according to the invention
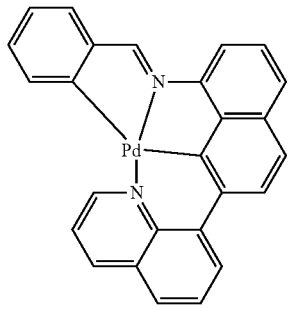
76
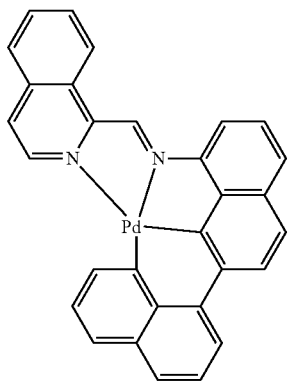
77
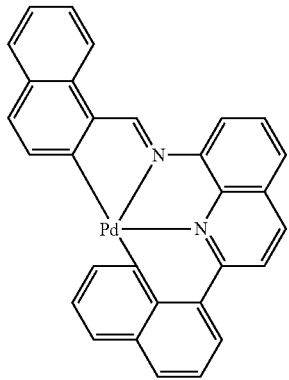
78
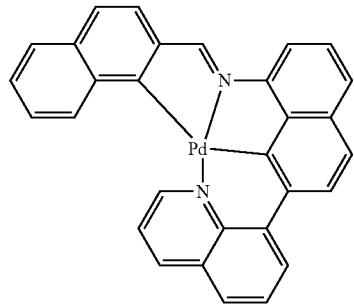
79

TABLE 1-continued
Examples of compounds of the formulae I to XVI according to the invention
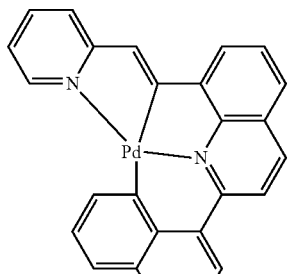
80
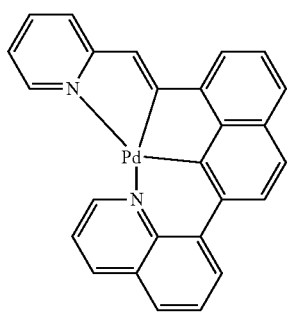
81
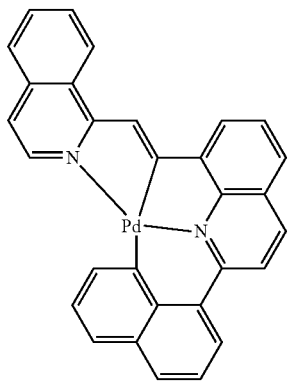
82
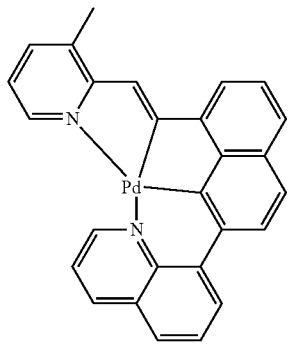
83

TABLE 1-continued
Examples of compounds of the formulae I to XVI according to the invention
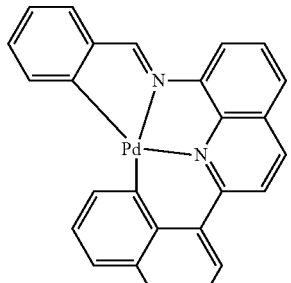
84
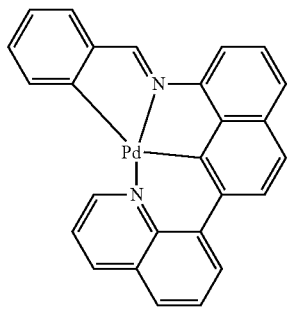
85
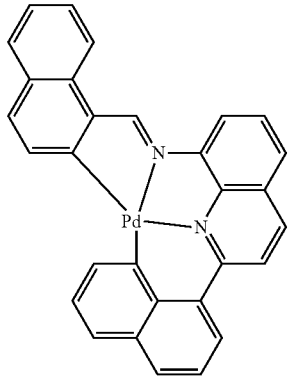
86
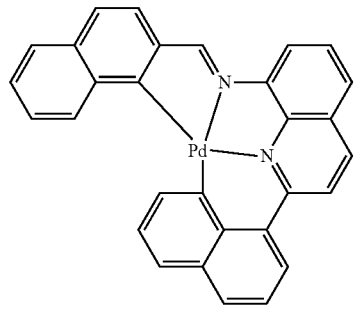
87

TABLE 1-continued
Examples of compounds of the formulae I to XVI according to the invention
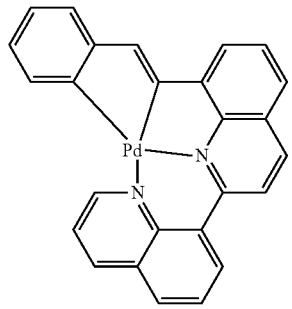
88
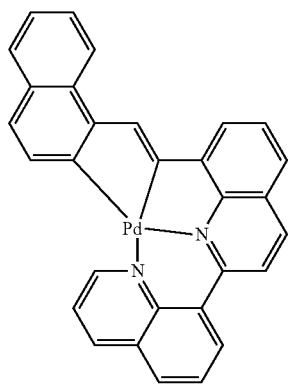
89
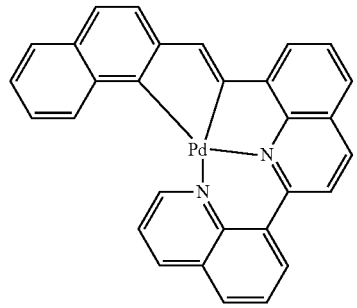
90
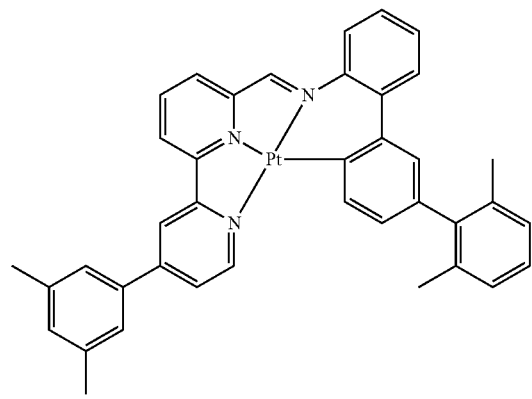
91

TABLE 1-continued
Examples of compounds of the formulae I to XVI according to the invention
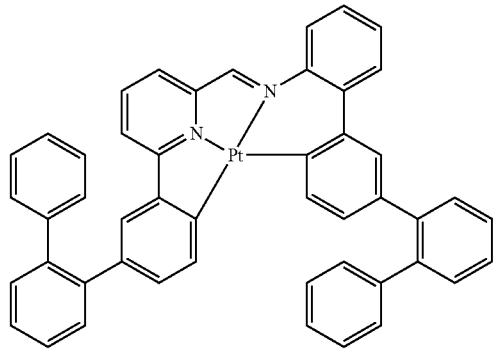
92
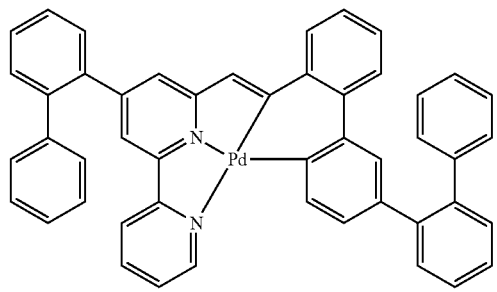
93
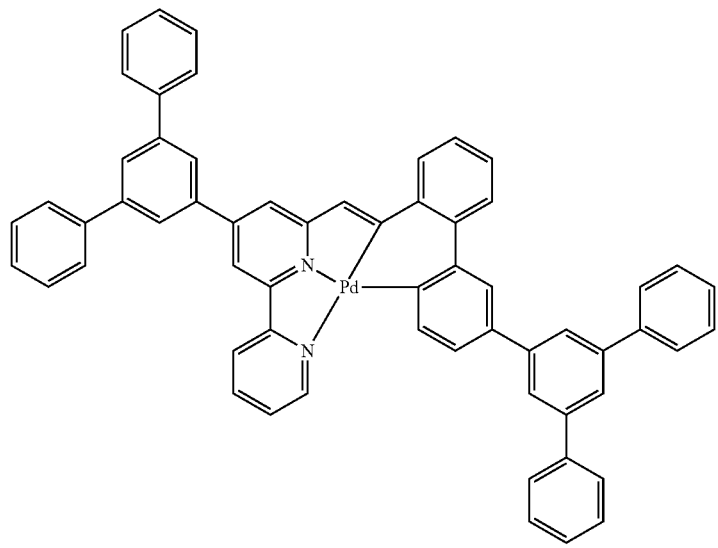
94

TABLE 1-continued

Examples of compounds of the formulae I to XVI according to the invention

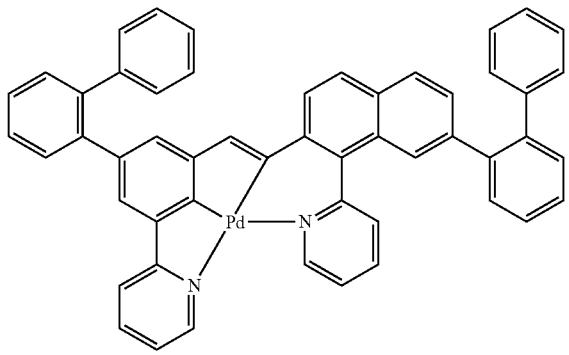

95

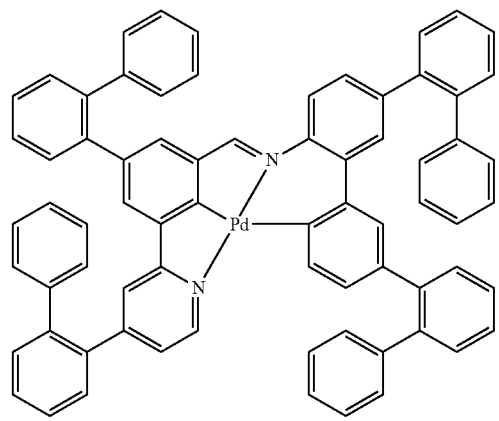

96

The compounds according to the invention are preferably square-planar complexes or approximately square-planar complexes which contain a tetracoordinated metal ion, in oxidation state +2. The metal is preferably selected from metals from group 10 of the Periodic Table of the Elements, in particular Pd and Pt. The compounds according to the invention have triplet emission and have a very good lifetime, high efficiency, high stability to temperature stresses and a high glass transition temperature Tg.

The invention also relates to a process for the preparation of a compound of the general formula I or II

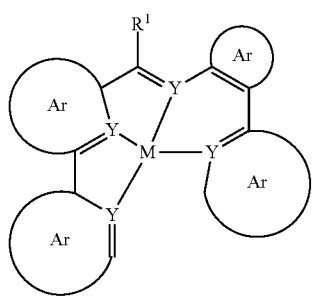

formula I

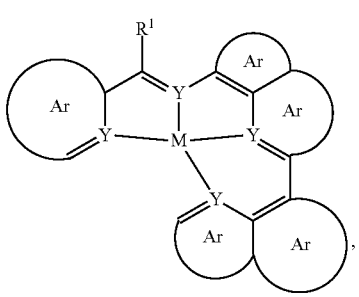

formula II where M, Y, Ar, R, $R^1$ and $R^2$ have the meaning defined above.

The compounds of the formula I or II according to the invention can be prepared by synthetic steps generally known to the person skilled in the art.

The starting point for the ligand synthesis can be, for example, 6-phenylpyridine-2-carboxaldehyde (J. Am. Chem. Soc. 2003, 125(8), 2113-2128), 2-biphenylamine (Tetrahedron Lett. 2008, 49(9), 1555-1558), 3-pyridin-2-yl-benzaldehyde (Org. Lett. 2004, 6(19), 3337-3340) or 2-chloro-8-nitroquinoline (Australian J. Chem. 2003, 56(1), 39-44).

A first step involves the synthesis of the corresponding part-ligands, which are combined in a further step to give the desired ligand system. A reaction is subsequently carried out with the corresponding metal (for example Pt or Pd), which is usually employed as a solution of a suitable metal salt, for example $K_2PtCl_4$ or $K_2PdCl_4$.
A general synthetic procedure for the preparation of the metal complexes of the formula I or II is depicted in schemes 1 to 4. The central metal Pt here can be replaced by Pd in analogous reactions.
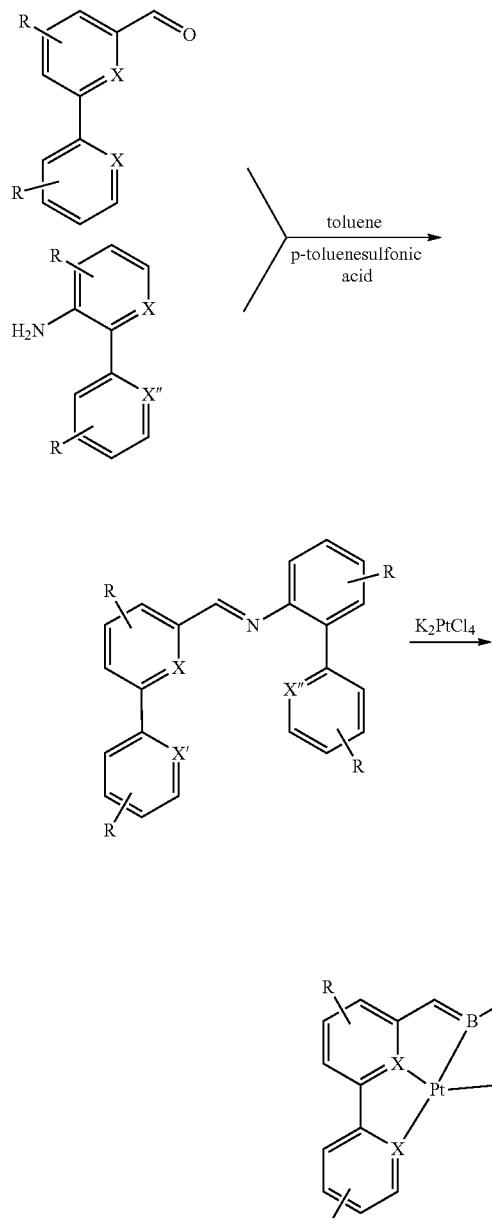
Scheme 1
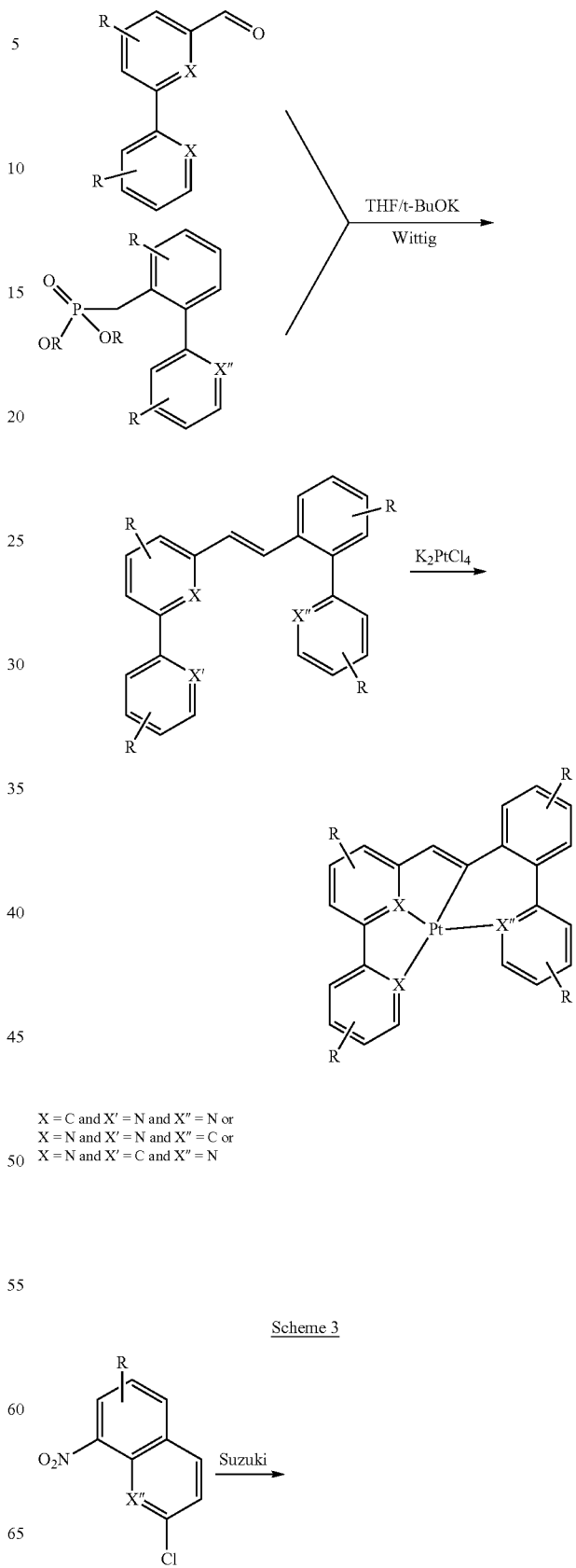
Scheme 2
Scheme 3

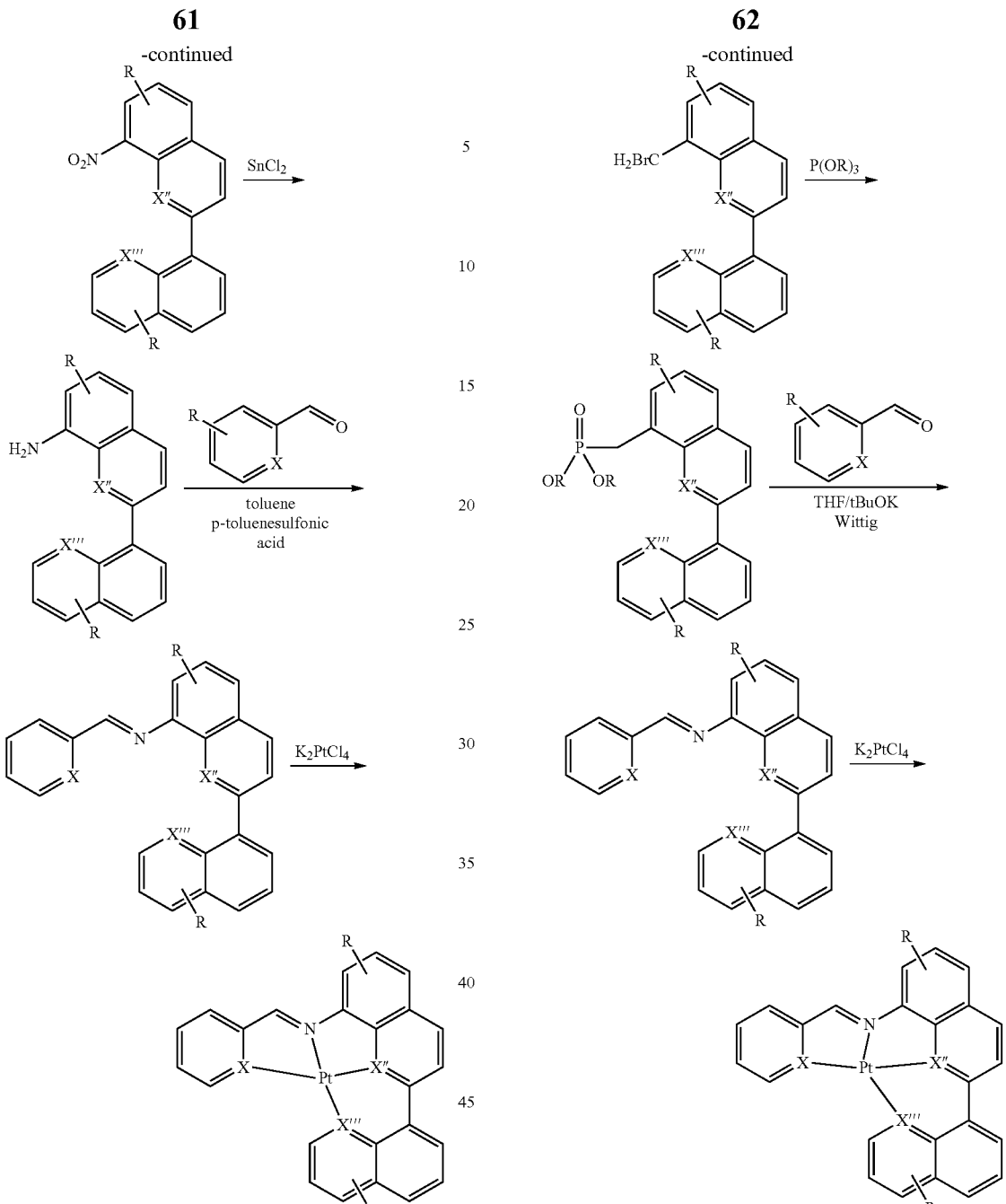

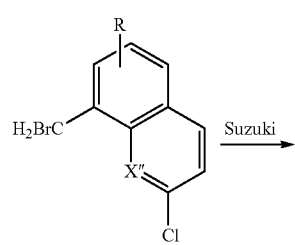

Scheme 4

The invention also relates to the use of the compounds according to the invention in an organic electronic device. The organic electronic device used in accordance with the invention can be organic electroluminescent devices (OLEDs) or polymeric electroluminescent devices (PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (=Organic light-emitting diodes, OLEDs, PLEDs).

In particular, the invention relates to the use of the compounds according to the invention as emitter compound and/or as charge-transport material and/or charge-injection material, preferably in a corresponding layer. This can be either a hole-transport layer, hole-injection layer, electron-transport layer or electron-injection layer. The use as charge-blocking material is also possible, depending on the structure.

The invention likewise relates to organic electronic devices, such as, for example, organic electroluminescent devices or polymeric electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (=Organic light-emitting diodes, OLEDs, PLEDs), comprising one or more compounds of the formula I or II, as defined above. For the purposes of this invention, an organic electronic device is taken to mean an electronic device comprising an anode, cathode and at least one layer which comprises at least one organic material. The device here may also comprise inorganic materials in addition to the organic material.

The compound of the formula I or II is preferably present within one layer in the electronic device.

The invention thus also relates to a layer comprising a compound of the formula I or II, as defined above.

The organic electroluminescent device comprises a cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). It is likewise possible for interlayers, which have, for example, an exciton-blocking function, to be introduced between two emitting layers. However, it should be pointed out that each of these layers does not necessarily have to be present. These layers may comprise compounds of the general formula I or II, as defined above.

In a preferred embodiment of the invention, the compound of the formula I or II is employed as emitting compound in an emitting layer or as charge-transport compound. The organic electroluminescent device here may comprise one emitting layer or a plurality of emitting layers, where at least one emitting layer comprises at least one compound of the formula I or II, as defined above. If a plurality of emission layers are present, these preferably have a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure, see, for example, WO 05/011013).

If the compound of the formula I or II is employed as emitting compound in an emitting layer, it is preferably employed in combination with one or more compounds functioning as matrix. In these cases, the mixture comprising the compound of the formula I or II and the matrix material comprises between 1 and 99% by weight, preferably between 2 and 90% by weight, particularly preferably between 3 and 40% by weight, in particular between 5 and 15% by weight, of the compound of the formula I or II, based on the entire mixture comprising emitter and matrix material. Correspondingly, the mixture comprises between 99 and 1% by weight, preferably between 98 and 10% by weight, particularly preferably between 97 and 60% by weight, in particular between 95 and 85% by weight, of the matrix material, based on the entire mixture comprising emitter and matrix material.

Preferred matrix materials are aromatic ketones, aromatic phosphine oxides or aromatic sulfoxides or sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with the unpublished application DE 102008036982.9, WO 07/063,754 or WO 08/056,746, zinc complexes, for example in accordance with EP 652273 or WO 09/062,578, or diazasilole or tetraazasilole derivatives, for example in accordance with the unpublished application DE 102008056688.8.

A further preferred embodiment of the invention is the use of the compound of the formula I or II as emitter material in combination with two or more different matrix materials. Suitable matrix materials in these cases are the preferred compounds mentioned above.

Preference is furthermore given to an organic electroluminescent device in which one or more layers are applied by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, if necessary, by suitable substitution, are necessary for this purpose.

These processes are generally known to the person skilled in the art and can be applied by him without problems to organic electroluminescent devices comprising compounds of the formula I or II, as defined above.

The compounds according to the invention described above, in particular compounds which are substituted or functionalised by reactive groups, can be used as monomers for the preparation of corresponding oligomers, dendrimers or polymers.

The invention therefore furthermore relates to oligomers, polymers or dendrimers comprising one or more compounds of the formula I or II, as defined above, where one or more bonds are present from the compounds of the formula I or II to the polymer, oligomer or dendrimer. Depending on the linking of the compound of the formula I or II, the complex therefore forms a side chain of the oligomer or polymer or is linked in the main chain. The polymers, oligomers or dendrimers may be conjugated, partially conjugated or non-conjugated. The oligomers or polymers may be linear, branched or dendritic.

For the preparation of the oligomers or polymers, the functionalised compounds of the formula I or II are homopolymerised or copolymerised with further monomers. Preference is given to copolymers, where the compounds of the formula I or II are present to the extent of 0.01 to 50 mol %, particularly preferably in the range from 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The proportion of these units in total is preferably in the region of at least 50 mol %. The polymers, oligomers and dendrimers may also contain further units, for example hole-transport units, in particular those based on triarylamines, and/or electron-transport units.

Polymers comprising compounds of the general formula I or II can be used for the production of PLEDs, in particular as emitter layer in PLEDs. A polymeric emitter layer can be produced, for example, by coating from solution (spin coating or printing processes).

The compounds according to the invention and the organic electroluminescent devices produced therewith are distinguished by the following surprising advantages over the prior art:

In contrast to many metal complexes in accordance with the prior art, which undergo partial or complete pyrolytic decomposition on sublimation, the compounds according to the invention have high thermal stability.

The use of bulky substituents on the aromatic or heteroaromatic ring systems prevents aggregation of the complexes and thus the formation of excimers or exciplexes to be substantially suppressed.

Organic electroluminescent devices comprising compounds of the formula I or II as emitting materials have an excellent lifetime.

Blue-, red- and green-phosphorescent complexes which have an efficient dark-blue, red or even green emission colour and have a long lifetime on use in organic electroluminescent devices are accessible. This is a significant advance over the prior art, since blue-, red- and green-phosphorescent devices were hitherto frequently accessible with poor colour coordinates and in particular a poor lifetime.

The compounds according to the invention, employed in organic electroluminescent devices, result in high efficiencies and steep current-voltage curves at the same time as low use voltages.

These above-mentioned advantages are not accompanied by an impairment of the other electronic properties.

The invention is explained in greater detail by the following examples, without wishing to restrict it thereby. The person skilled in the art will be able to synthesise further compounds according to the invention without inventive step and employ them in organic electroluminescent devices.

EXAMPLES

The following syntheses are carried out under a protective-gas atmosphere in dried solvents, unless indicated otherwise. The starting materials used are, for example, 6-phenylpyridine-2-carboxaldehyde (J. Am. Chem. Soc. 2003, 125(8), 2113-2128), 2-biphenylamine (Tetrahedron Lett. 2008, 49(9), 1555-1558), 3-pyridin-2-ylbenzaldehyde (Org. Lett. 2004, 6(19), 3337-3340), 2-chloro-8-nitroquinoline (Australian J. Chem. 2003, 56(1), 39-44).

Example 1

Synthetic Procedure for Metal Complex (1)

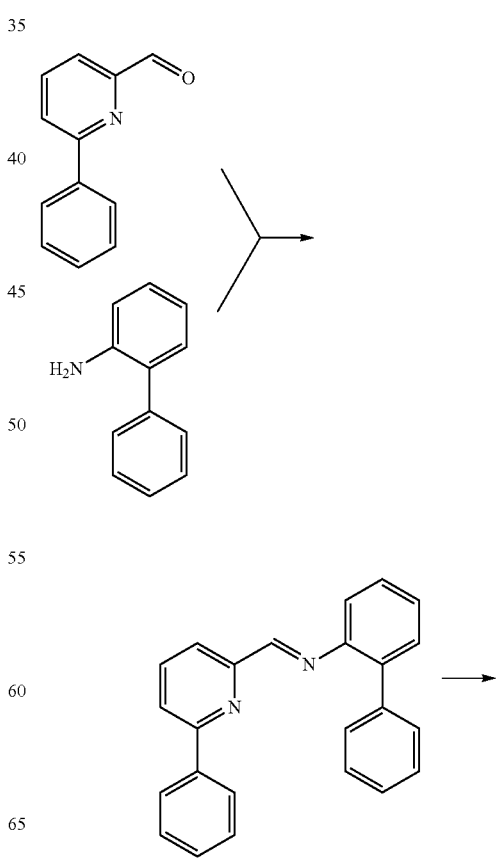

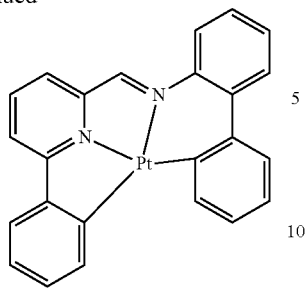

1st Step: Ligand Synthesis

The ligand synthesis is carried out utilising azeotropic distillation for removal of the water formed. Firstly, 300 ml of dried toluene are heated to the boil in a distillation apparatus in a 500 ml three-necked flask with stirrer, internal thermometer and dropping funnel. A solution of 20 g (120 mmol) of 2-biphenylamine in 50 ml of dried toluene and a solution of 21.9 g (120 mmol) of 6-phenylpyridine-2-carboxaldehyde in 50 ml of toluene are subsequently slowly added dropwise. Catalytic amounts of p-toluenesulfonic acid are added to the mixture. The distillation is carried out until the clear condensed toluene appears. The residues of the solvent are removed in an oil-pump vacuum (130 Pa). The ligand is recrystallised from toluene and washed with MeOH, giving 31.5 g (94 mmol) of crystalline solid. The overall yield is 80%.

2nd Step: Complex Synthesis

A solution of 13.8 g (41.5 mmol) of imine ligand in 1300 ml of acetic acid is added to a solution of 17.2 g of K$_2$PtCl$_4$ (41.5 mmol) in 1300 ml of acetic acid under N$_2$, and the mixture is stirred at 90° C. for 3 days. After 72 h, the precipitated solid is washed with cold methanol, dried in vacuo and subsequently recrystallised from absolute EtOH under a protective gas, giving 15.9 g (30 mmol) of crystalline solid. The overall yield is 73%.

Example 2

Synthetic Procedure for Metal Complex (8)

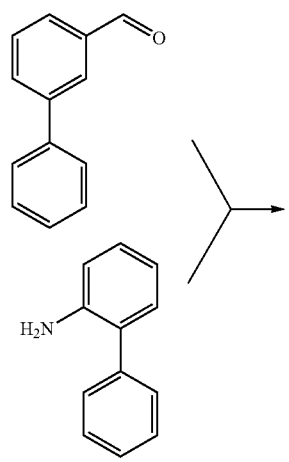

1st Step: Ligand Synthesis

The ligand synthesis is carried out utilising azeotropic distillation for removal of the water formed. Firstly, 300 ml of dried toluene are heated to the boil in a distillation apparatus in a 500 ml three-necked flask with stirrer, internal thermometer and dropping funnel. A solution of 20 g (120 mmol) of 2-biphenylamine in 50 ml of dried toluene and a solution of 21.9 g (120 mmol) of 3-pyridin-2-ylbenzaldehyde in 50 ml of toluene are subsequently slowly added dropwise. Catalytic amounts of p-toluenesulfonic acid are added to the mixture. The distillation is carried out until the clear condensed toluene appears. The residues of the solvent are removed in an oil-pump vacuum (130 Pa). The ligand is recrystallised from toluene and washed with MeOH, giving 30.1 g (90 mmol) of crystalline solid. The overall yield is 76%.

2nd Step: Complex Synthesis

A solution of 13.8 g (41.5 mmol) of imine ligand in 1300 ml of acetic acid is added to a solution of 17.2 g of K$_2$PtCl$_4$ (41.5 mmol) in 1300 ml of acetic acid under N$_2$, and the mixture is stirred at 90° C. for 3 days. After 72 h, the precipitated solid is washed with cold methanol, dried in vacuo and subsequently recrystallised from absolute EtOH under a protective gas, giving 14.3 g (27 mmol) of crystalline solid. The overall yield is 66%.

Example 3

Synthetic Procedure for Metal Complex (30)

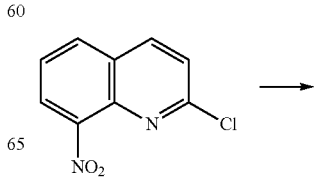

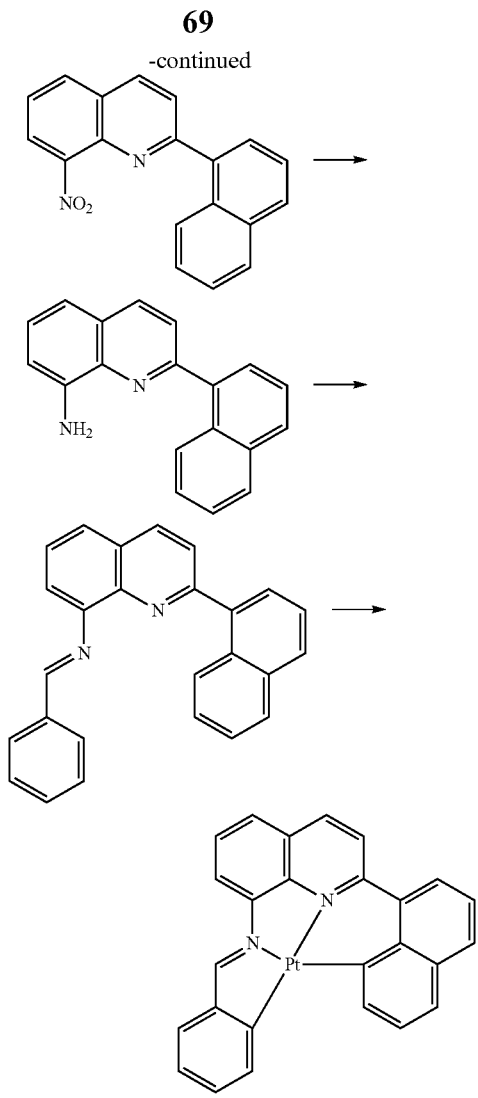

1st Step: 8-Nitro-2-naphthylquinoline 18.9 g (110.0 mmol) of 1-naphthylboronic acid, 22.9 g (110.0 mmol) of 2-chloro-8-nitroquinoline and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water and subsequently evaporated to dryness. The yield is 26.4 g (87 mmol), corresponding to 80% of theory.

2nd Step: 8-Amino-2-naphthylquinoline 12.6 g (42 mmol) of 8-nitro-2-naphthylquinoline and 1.99 g of Pd/C (10%) are suspended in 200 ml of methanol. 8.4 g (222 mmol) of sodium borohydride are added in portions with stirring at 0° C. After stirring for 2 h, the clear solution is neutralised using dilute HCl. The solvent is then removed, and the resultant residue is washed vigorously with water and recrystallised from dioxane. The precipitate is filtered and dried in vacuo, giving 9.9 g (56.9 mmol) of crystalline solid. The overall yield is 88%.

3rd Step: 1-[(E)-8-Quinolinylimino)methyl]naphthalene

The ligand synthesis is carried out utilising azeotropic distillation for removal of the water formed. Firstly, 300 ml of dried toluene are heated to the boil in a distillation apparatus in a 500 ml three-necked flask with stirrer, internal thermometer and dropping funnel. A solution of 32.4 g (120 mmol) of 8-amino-2-naphthylquinoline in 50 ml of dried toluene and a solution of 12.7 g (120 mmol) of benzaldehyde in 50 ml of toluene are subsequently slowly added dropwise. Catalytic amounts of p-toluenesulfonic acid are added to the mixture. The distillation is carried out until the clear condensed toluene appears. The residues of the solvent are removed in an oil-pump vacuum (130 Pa). The ligand is recrystallised from toluene and washed with MeOH, giving 32.1 g (89 mmol) of crystalline solid. The overall yield is 75%.

4th Step: Complex Synthesis

A solution of 14.8 g (41.5 mmol) of imine ligand in 1300 ml of acetic acid is added to a solution of 17.2 g of $K_2PtCl_4$ (41.5 mmol) in 1300 ml of acetic acid under $N_2$, and the mixture is stirred at 90° C. for 3 days. After 72 h, the precipitated solid is washed with cold methanol, dried in vacuo and subsequently recrystallised from absolute EtOH under protective gas, giving 13.4 g (24 mmol) of crystalline solid. The overall yield is 59%.

Example 4

Production and Characterisation of Organic Electroluminescent Devices

Electroluminescent devices according to the invention can be produced as described, for example, in WO 05/003253. The results for various OLEDs are compared here. The basic structure, the materials used, the degree of doping and their layer thicknesses are identical for better comparability. The first device example describes a comparative standard in accordance with the prior art, in which the emission layer consists of the host material spiro-ketone and the guest material (dopant) Ir(piq)$_3$ or a compound according to the invention. Furthermore, OLEDs having various structures are described, with the host material in each case being spiro-ketone. OLEDs having the following structure are produced analogously to the general process mentioned above:

| | |
|---|---|
| Hole-injection layer (HIL) | 20 nm of 2,2',7,7'-tetrakis(di-para-tolyl-amino)spiro-9,9'-bifluorene |
| Hole-transport layer (HTL) | 20 nm of NPB (N-naphthyl-N-phenyl-4,4'-diaminobiphenyl) |
| Emission layer (EML) | 40 nm of host: spiro-ketone (SK) (bis(9,9'-spirobifluoren-2-yl) ketone) |
| | Dopant: Ir(piq)$_3$ (10% doping, vapour-deposited; synthesised in accordance with WO 03/0068526) or compounds according to the invention |
| Electron conductor (ETL) | 20 nm of AlQ$_3$ (tris(quinolinato)aluminium-(III)) |
| Cathode | 1 nm of LiF, 150 nm of Al on top. |

The structures of Ir(piq)₃ and spiro-ketone are depicted below for clarity:

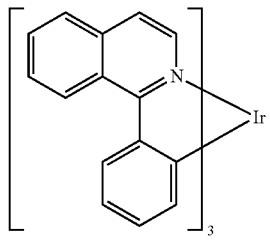

Ir(piq)₃

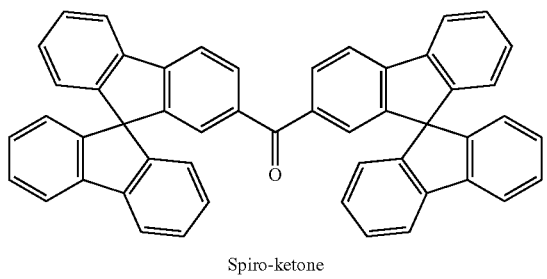

Spiro-ketone

The compounds according to the invention are depicted below:

Example 1

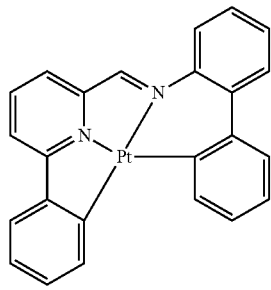

Example 3

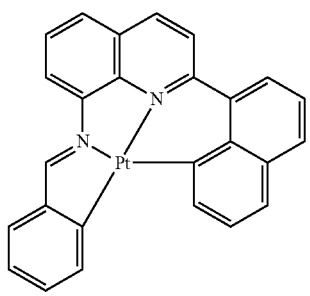

These as yet unoptimised OLEDs are characterised by standard methods. For this purpose, the electroluminescence spectra, the efficiency (measured in cd/A) as a function of the luminance, calculated from current-voltage-luminance characteristic lines (IUL characteristic lines), and the lifetime are determined.

Table 2 shows the results of the device measurement. The electroluminescent devices comprising the compounds according to the invention exhibit a longer lifetime with improved efficiency.

TABLE 2

Device results with spiro-ketone as host material and with Ir(piq)₃ or compounds according to the invention as dopant

| Ex. | EML | Max. efficiency [cd/A] | Voltage at 1000 cd/m² | CIE (x, y) | Lifetime, initial luminance 1000 cd/m² |
|---|---|---|---|---|---|
| 4a (comp.) | SK: 10% Ir(piq)₃ | 8 | 5.0 | 0.68/0.32 | 30000 |
| 4b | SK: 10% Ex. 1 | 8.5 | 5.2 | 0.68/0.32 | 36000 |
| 4c | SK: 10% Ex. 3 | 22 | 5.3 | 0.62/0.38 | 25000 |

The invention claimed is:

1. A compound of the general formula I

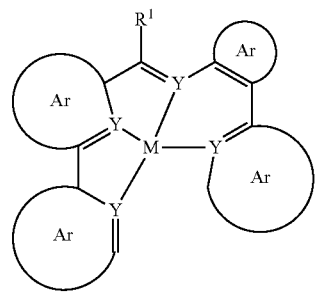

formula I or of the general formula II

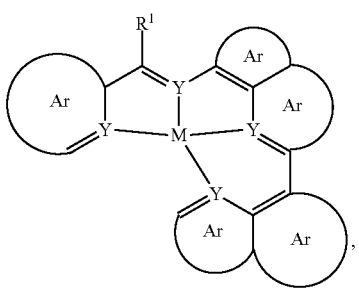

formula II wherein

M is a metal ion in oxidation state +2,

Ar, is, identically or differently on each occurrence, an aromatic or heteroaromatic ring system having 5 to 10 aromatic ring atoms, which is optionally substituted by a plurality of radicals R, R is, identically or differently on each occurrence, H, D, F, Cl, Br, I, $N(Ar^1)_2$, $N(R^2)_2$, CN, $NO_2$, $Si(R^2)_3$, $B(OR^2)_2$, $C(=O)Ar^1$, $C(=O)R^2$, $P(=O)(Ar^1)_2$, $P(=O)(R^2)_2$, $S(=O)Ar^1$, $S(=O)R^2$, $S(=O)_2Ar^1$, $S(=O)_2R^2$, $CR^2=CR^2Ar^1OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, C=O, O, or S and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 15 aromatic ring atoms, which is optionally substituted by one or more radicals $R^2$, or a combination of these systems, where two or more substituents R optionally forms a mono- or polycyclic, aliphatic or aromatic ring system with one another, $Ar^1$ is, identically or differently on each occurrence, an aromatic or heteroaromatic ring system having 5 to 40 aromatic ring atoms, which is optionally substituted by one or more non-aromatic radicals R, Y is, identically or differently on each occurrence, C, N or P, with the proviso that either two C atoms and two N atoms or two C atoms and two P atoms are always bonded to the metal, and $R^1$ is, identically or differently on each occurrence, H, D, F, $CF_3$, CN, an alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which is optionally substituted by one or more radicals $R^2$, or a combination of these systems, where $R^1$ may also form a mono- or polycyclic, aliphatic or aromatic ring system with R, and $R^2$ is, identically or differently on each occurrence, H, D, F, CN or an aliphatic, aromatic and/or heteroaromatic hydrocarbon radical having 1 to 20 C atoms, in which, in addition, one or more H atoms is optionally replaced by F, where two or more substituents $R^2$ also form a mono- or polycyclic, aliphatic or aromatic ring system with one another.

2. The compound according to claim 1, wherein M is Pt or Pd.

3. The compound according to claim 1, wherein M is Pt.

4. The compound according to claim 1, wherein

M is Pt,

Y is, identically or differently on each occurrence, C or N, with the proviso that two C atoms and two N atoms are always bonded to the metal, R is, identically or differently on each occurrence, H, $N(Ar^1)_2$, CN, a straight-chain alkyl group having 1 to 10 C atoms or an aromatic or heteroaromatic ring system having 5 to 15 aromatic ring atoms, each of which is optionally substituted by one or more radicals $R^2$, $R^1$ is, identically or differently on each occurrence, H, D, CN, an alkyl group having 1 to 3 C atoms or an aromatic or heteroaromatic ring system having 5 to 10 aromatic ring atoms, each of which is optionally substituted by one or more radicals $R^2$, $R^2$ is, identically or differently on each occurrence, H, F, CN or an aliphatic, aromatic and/or heteroaromatic hydrocarbon radical having 1 to 20 C atoms, where two or more substituents $R^2$ may also form a mono- or polycyclic, aliphatic or aromatic ring system with one another, and $Ar^1$ is, identically or differently on each occurrence, an aromatic or heteroaromatic ring system having 5 to 40 aromatic ring atoms, which is optionally substituted by one or more non-aromatic radicals R.

5. The compound according to claim 1, wherein Ar is benzene, naphthalene, pyridine, pyrimidine, pyrazine, pyridazine, quinoline, isoquinoline, furan, thiophene, pyrrole, benzofuran, benzothiophene or indole.

6. The compound according to claim 1, wherein Ar is benzene, naphthalene, pyridine, quinoline or isoquinoline.

7. The compound according to claim 1, wherein the compound is of the formulae V to XVI:

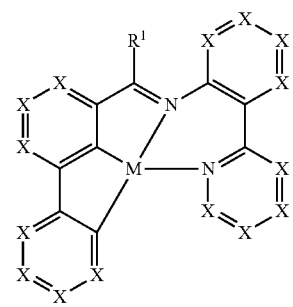

formula V

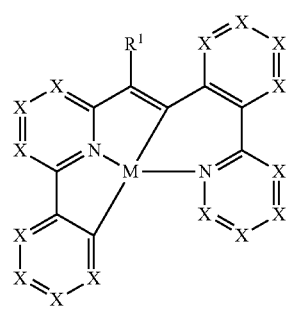

formula VI

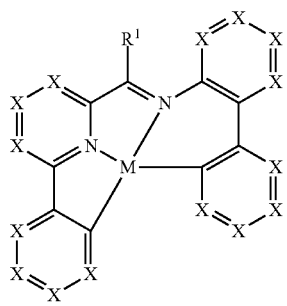

formula VII

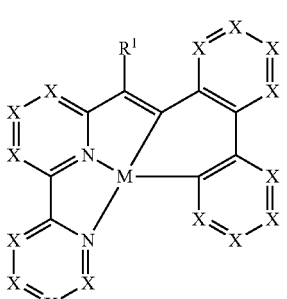

formula VIII formula IX
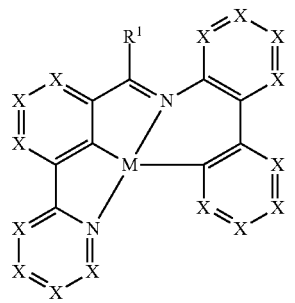

formula X
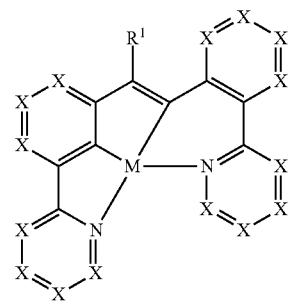

formula XI
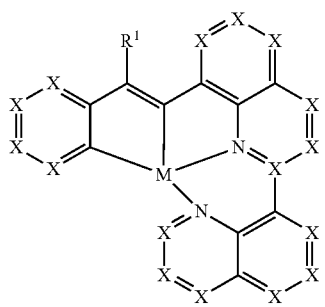

formula XII
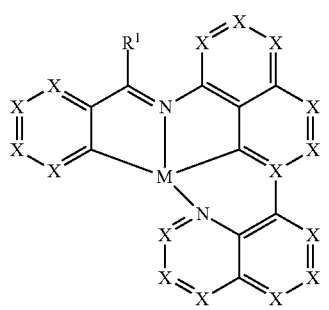

formula XIII
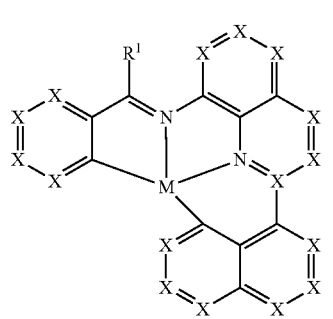

formula XIV
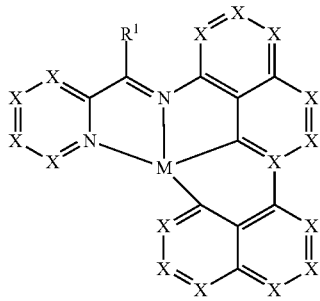

formula XV
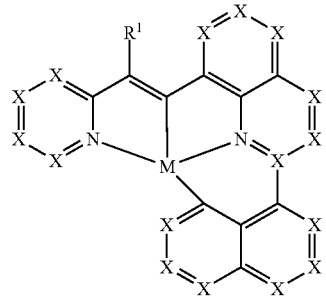

formula XVI
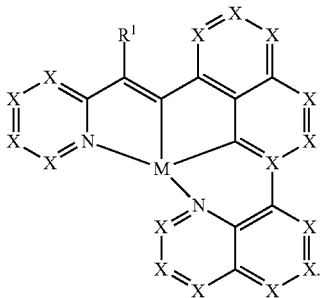

8. A oligomer, polymer or dendrimer comprising one or more compounds according to claim 1, where one or more bonds are present from the compounds of the formula I or II to the polymer, oligomer or dendrimer.

9. A process for the preparation of the compound according to claim 1, which comprises reacting a free ligand with a corresponding metal salt to give the complex.

10. A layer comprising one or more of the compounds according to claim 1.

11. The compound according to claim 1, wherein the compound is of the formula III or IV:

formula III
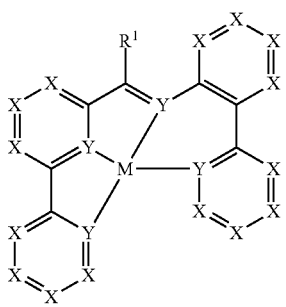

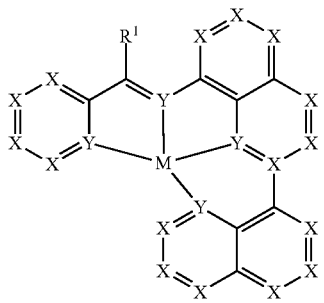

formula IV wherein
X is CR or N.

12. The compound according to claim 11, wherein a maximum of two symbols X per ring stand for N and the other symbols X in this ring stand for CR.

13. An electronic device comprising one or more compounds according to claim 1.

14. The electronic device as claimed in claim 13, wherein the electronic device is an organic electroluminescent device or polymeric electroluminescent device (OLED, PLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diods (O-laser).

15. An organic electroluminescent device according to claim 14, wherein the compound is employed as emitting compound in an emitting layer or as charge-transport compound in a charge-transport or charge-injection layer.

* * * * *